United States Patent [19]
Honeycutt et al.

[11] Patent Number: 5,972,039
[45] Date of Patent: Oct. 26, 1999

[54] INCREASED ABSORBENCY AND HAND-FEEL FABRICS

[75] Inventors: Travis W. Honeycutt, Gainesville; Baosheng Lee, Duluth; Dong Dai, Lawrenceville; Nigel J. Flynn, Duluth, all of Ga.

[73] Assignee: Isolsyer Company, Inc., Norcross, Ga.

[21] Appl. No.: 08/835,223

[22] Filed: Apr. 7, 1997

[51] Int. Cl.⁶ .................................................. D06M 10/02
[52] U.S. Cl. ........................... 8/115.52; 134/42; 427/533; 427/535; 427/536; 427/538; 442/102; 442/164; 442/165; 442/166; 442/168; 442/59; 442/1; 442/2; 442/43; 428/375; 428/365; 428/364; 428/357; 604/358
[58] Field of Search ............................. 8/115.52; 134/42; 427/533, 535, 536, 538; 442/102, 167, 165, 166, 168, 59, 1, 2, 43, 58; 428/375, 365, 364, 357; 604/358

[56] References Cited

U.S. PATENT DOCUMENTS

| | | |
|---|---|---|
| 2,639,970 | 5/1953 | Tomonari . |
| 3,053,605 | 9/1962 | Tanabe et al. . |
| 3,111,363 | 11/1963 | Nasuno . |
| 3,817,701 | 6/1974 | Thorsen . |
| 4,601,911 | 7/1986 | Ueno et al. ............................. 427/538 |
| 5,181,966 | 1/1993 | Honeycutt et al. . |
| 5,207,837 | 5/1993 | Honeycutt ................................. 134/42 |
| 5,354,259 | 10/1994 | Scholz et al. . |
| 5,405,643 | 4/1995 | Scholz . |
| 5,455,108 | 10/1995 | Quincy et al. ........................... 428/266 |
| 5,470,653 | 11/1995 | Honeycutt et al. ..................... 428/357 |
| 5,474,522 | 12/1995 | Scholz et al. . |
| 5,498,232 | 3/1996 | Scholz . |
| 5,620,786 | 4/1997 | Honeycutt et al. ....................... 442/50 |

FOREIGN PATENT DOCUMENTS

| | | |
|---|---|---|
| 0 484 830 | 5/1992 | European Pat. Off. . |
| 484830 | 5/1992 | European Pat. Off. . |
| 0 492 649 | 7/1992 | European Pat. Off. . |
| 1312431 | 4/1973 | United Kingdom . |
| 1517489 | 7/1978 | United Kingdom . |
| 1 517 489 | 7/1998 | United Kingdom . |
| WO 96 27044 | 9/1996 | WIPO . |
| WO 96 28597 | 9/1996 | WIPO . |
| WO 96/28597 | 9/1996 | WIPO . |

OTHER PUBLICATIONS

Corona Treatment, Theory—A Summary, by Pillar Technologies Ltd. Partnership (Date Unknown).

Compressive Treatment Process, Product Brochure by Micrex Corporation (Date Unknown).

Corona Treating of Substrates, by Derwin L. Whiteside (Reprinted from 1985 Polymers, Laminations and Coatings Conference) (1985) (Month Unknown).

Increasing the Wettability of Film & Foil Webs: Part II, by Herbert Weiss (Date Unknown).

*Primary Examiner*—Alan Diamond
*Attorney, Agent, or Firm*—Needle & Rosenberg, P.C.

[57] ABSTRACT

A method for enhancing the absorbency, hand-feel, or both of an article made from fibers having a spin finish thereon, where the spin finish decreases the hand-feel desirability and decreases the absorbency of the article. The method involves subjecting the article to corona treatment for a period of time sufficient to enhance the absorbency, hand-feel, or both of the article. The article produced by subjecting a substrate made of fibers having a finish thereon to corona treatment for a period of time sufficient to enhance the absorbency, hand-feel, or both of the substrate. A method of disposing of such articles by contacting the articles with a hot liquid, such as water, for a period of time sufficient to disperse or dissolve the article. Hot water soluble, cold water insoluble poly(vinyl) alcohol is one suitable fiber material.

39 Claims, No Drawings

INCREASED ABSORBENCY AND HAND-FEEL FABRICS

BACKGROUND OF THE INVENTION

I. Field of the Invention

The present invention relates to the field of fabrics and, particularly, to absorbent fabrics of improved absorbency and hand-feel.

II. Background of the Invention

Hospital patient care generates considerable quantities of infectious medical waste in primary and acute care facilities. Such facilities have a need to provide various textile products to be used by physicians and other professionals, as well as for bedding, draperies, towels, and similar items.

At one time, virtually all textiles used in such environments were reusable. Reusable textiles, were primarily made from woven fabrics of yams and the yams were composed of cotton or other natural fibers. However, synthetics were later developed which included fibers such as nylon, rayon and polyester. These synthetics were primarily spun from staple fibers and very little texturized synthetic filaments were in use at that time.

Approximately thirty years ago, disposable garments, covers, linens and drapes were introduced to the medical environment. When compared to the reusable garments, the disposables offered many cost- and time-saving features. For instance, hospitals were able to reduce or entirely eliminate their laundry facilities and the hospital had, for the first time, garments that exhibited significant barrier protection. Barrier protection is important in hospitals to prevent unwanted contact of the wearer to harmful liquids, infections agents, and other bodily fluids.

Another significant drawback to reusable textiles was that they could not provide liquid barrier capabilities, especially after only a few laundry cycles. However, the average lifetime of a hospital reusable was approximately 18 laundry cycles.

Current disposables are generally non-woven in composition. For instance, carded stock is often chemically bonded into fabrics. Such carded webs are treated with adhesives or bonding agents and are then calendared to form "paper-light" materials. Carded webs have recently been replaced by thermobond materials, which have a softer "hand," but which have reduced cross-directional strength.

Further current disposables are produced from air-entangled and hydroentangled fibers which produce suitable fabrics. Such non-wovens are composed mostly of polypropylene fibers or from a polyester staple with cellulose wood pulp. These hydroentangled webs display the most textile-like hand, as well as a high degree of dimensional or cross-directional strength. Non-wovens of this class, such as SONTARA® by Du Pont, are widely accepted for use in medical gowns and drapes.

Recently, the medical industry has begun reverting to the use of reusable items. This trend arose because the disposable items produced significant infectious waste products. Originally, disposables were favored because they promoted anti-septic patient contact and decreased the potential for cross-infections between patients, a significant problem with cleanable, reusable textiles. However, various federal and state regulations have subsequently reclassified much of the disposable product as "infectious," thereby making desirable the minimization of their use.

An average hospital patient produces 55 lbs. of medical waste per day. Approximately 20% of that waste is classified as "infectious." The American Hospital Association and the Centers for Disease Control recommend immediate disposal of medical waste. Medical waste is considered an occupational hazard for health care workers, but is not considered an environmental safety problem. The most preferable way to contain infectious medical waste is to disinfect it at the point of generation and dispose of the treated medical waste with minimum handling and storage on premises.

The need for an effective way to dispose of medical waste has been highlighted by the amendment made to 29 C.F.R. § 1910.1030 which provides for the federal regulation under the Occupational Safety and Health Act, 29 U.S.C. § 655, 657 (the "Act") to control blood borne pathogens. Specifically, the Act calls for the establishment of an exposure control plan, the containment of specimens of blood or other potentially infectious materials and the general tightening of precautionary measures to minimize the spread of disease. A safe and effective way to dispose of hospital waste is, Therefore, highly desirable because it would facilitate compliance with the Act.

As a result, consumption of medical disposable woven or non-woven products has been growing at a rate of approximately 10% a year. In 1988, sales totaled approximately 1.155 billion dollars. As of the end of 1996, sales of medical disposable non-woven products are believed to have exceeded two and a half billion dollars. In the United States, there are at least 30 million surgical procedures performed each year. After each surgical procedure, it is necessary that the operating theater be disinfected before a new procedure is performed to minimize any exposure the patients may bring to other patients or staff. This is particularly important in light of today's increasingly stringent regulations regarding occupational exposure to blood and bodily fluids.

Towels, sponges, and gauze have been in use since the first days of surgical procedures. They are used either to manipulate tissue, absorb blood and other oxidants of the wound site, as well as being used to clean hands and assist in cleaning certain utensils used in various surgical procedures. Traditionally, towels, sponges, and gauze have been made from cotton fibers, though in recent years attempts have been made to provide replacements from other fibers including polyesters, rayon and other staple materials. These fibers were chosen because of their relative availability and cleanliness as main-made materials. Cotton, on the other hand, is an agricultural material having volatile price and availability fluctuations. It has been noted that cotton replacements have, by and large, been unsatisfactory, although many attempts have been made to mimic the appearance of cotton.

Hospitals generally discard gauze, sponges and towels after each surgical use. Disposal takes place in either a landfill or by incineration. In either case, the handling of such articles after use promotes the exposure of certain blood borne diseases to those employees who are charged with the responsibility for bagging and introducing such materials into the disposal process.

It is thus an object of the present invention to provide suitable towels, sponges, gauze, as well as non-woven textiles capable of being disposed of after use while avoiding additional burdens being placed upon landfills and other disposal sites. It is yet a further object to provide suitable such articles which, after use, can be solubilized and substantially sterilized in a single operation.

SUMMARY OF THE INVENTION

The invention herein solves the drawbacks of the prior art by providing a textile suitable for use in the medical environment, such as for use as a towel, sponge, or gauze, which provides improved capability to absorbing harmful liquids and which provides a feel similar to that of traditional cotton fabrics.

The present invention provides a method for enhancing the absorbency, hand-feel, or both of an article (woven or non-woven) comprised of fibers having a finish thereon, the method comprising subjecting the article to corona treatment for a period of time sufficient to enhance the absorbency, hand-feel, or both of the article. The corona treatment can use an electric field operating at from about 1 to 5 kW of power, i.e., 40 to about 190 watt-min./sq. ft.

In another embodiment, the present invention provides an article produced by subjecting a substrate comprised of fibers having a finish thereon to corona treatment for a period of time sufficient to enhance the absorbency, hand-feel, or both of the substrate.

In yet another embodiment, the present invention provides a method of disposing of an article produced by subjecting a hot-liquid soluble, cold-liquid insoluble substrate comprised of fibers having a finish thereon to corona treatment for a period of time sufficient to enhance the absorbency, hand-feel, or both of the substrate, the method comprising contacting the article with a hot liquid for a period of time sufficient to disperse or dissolve the article.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE PREFERRED EMBODIMENTS

The present invention may be understood more readily by reference to the following detailed description of preferred embodiments of the invention.

Before the present methods and apparatuses are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

As used herein, the term "hot" is used to refer to temperatures above about body temperature, or 37° C. More preferably, "hot" refers to temperatures above 40° C., more preferably to temperatures above 45° C., even more preferably to temperatures above 50° C., even more preferably to temperatures above 75° C., and most preferably to temperatures above 90° C. Similarly, "cold" is used to refer to temperatures below about body temperature, or 37° C. More preferably, "cold" refers to temperatures below 30° C., more preferably to temperatures below 25° C., and even more preferably to temperatures below 20° C.

As used herein, the term "surgical fabric" refers to a textile like woven or non-woven article suitable for use in an operating room or other hospital or patient care setting. Such fabrics include, but are not limited to towels, sponges, gauzes, gowns, drapes, and masks.

As used herein, the term "hand-feel" refers generally to the undesirability of a fabric feeling slick or slimy to the touch as determined, inter alia, by the coefficients of friction of the fabric surface. For the purposes of the present invention, improved or enhanced hand-feel refers to the reduction of the slickness or sliminess feeling and similarly to the approximation of the feel of the fabric to the feel of cotton fabric of similar weave or knit.

As noted, the present invention pertains to fabrics such as towels, sponges, and gauze and methods for the disposal of such fabrics. These fabrics are used primarily in the medical industry in hospitals, outpatient facilities, and home environments. At such facilities, towels, sponges and gauze, particularly in surgical theaters, generally come into contact with human bodily fluids such that disposal and disinfection has become a matter of major concern in light of the lack of biodegradability of prior products and the potential spread of human borne diseases such as hepatitis B and AIDS. However, it should be noted that the fabrics could be used for a myriad of other uses not restricted to the health care industry, including any uses where hand-feel, increased absorbency, or hot water solubility of the fabric is desirable.

The fabrics can be natural or synthetic absorbent fabrics. The present invention is particularly effective for improving absorbency, hand-feel, or both of synthetic woven or non-woven fabrics which have been treated with processing chemicals that reduce the absorbency or degrade the hand-feel of the finished fabric. More preferably, the fabrics are such that it is undesirable to attempt to remove the finishing compounds by washing. Suitable fabrics include poly(vinyl) alcohol fabrics, rayon fabrics and polyester fabrics.

In order to cope with the medical environment in particular, suitable towels, sponges and gauze can be made from fibers comprising poly(vinyl) alcohol which is soluble in hot water only at temperatures above a predetermined temperature. Higher solubilization temperatures are used to prevent inadvertent solubilization while still permitting convenient disposal by the disposal methods of the invention.

In one embodiment, the fabrics are made from yarns made from a plurality of fibers of poly(vinyl) alcohol. The yarn can be formed as either a staple or as filament made from poly(vinyl) alcohol. This nontoxic, synthetic polymer is produced by alkali or acidic hydrolysis of polyvinyl acetate. The vinyl acetate monomer is produced by reacting either acetylene and acetic acid or ethylene, acetic acid and oxygen. Poly(vinyl) alcohol can be manufactured as a water soluble or insoluble resin. Water soluble resins of poly(vinyl) alcohol can be hot and cold water soluble or hot water soluble only. The temperature at which poly(vinyl) alcohol dissolves is controlled by changing its degree of hydrolysis and its polymer crystallinity and orientation.

Poly(vinyl) alcohol fibers used for the present invention are formed by dissolving suitable hot water soluble polyvinyl alcohol resin into deionized or distilled water to a 5% to 15% solids mixture, thereby creating a dope. The dope is then allowed to stand for a considerable amount of time, for example two weeks, for gel setting. It is desirable to maintain the dope free of microbial organisms because poly(vinyl) alcohol is subject to microbial degradation while in solution. Maintenance of the dope, therefore, is accomplished via ultrafiltration, heating, or other means known to one of ordinary skill in the art of preservation of resin solutions. Anti-microbial agents such as ester phenolic derivatives such as salicylic or benzoic esters can be used.

After the above-described resin has been gel set, it is then filtered and forced through a spinneret and into a saturated solution of sodium sulfate wherein the fibers are coagulated into a range of deniers of from 6 to 10. The fiber is then subjected to a drawing between a 2:1 and 5:1 ratio, with a 4:1 ratio being preferred and then the fiber is heat annealed to produce suitable hot water only soluble fibers. The fibers so produced are then either chopped into a staple between approximately 1" to 2" in length or are formed into two bundles which can then be stretch broken with a fiber length of 1" to 6". These fibers are then formed into a yarn either by conventional cotton spinning methods, woolen spinning methods or spun directly from the stretch broken tow. A preferred yarn size is between 60 to 0.5 singles, with up to four plies of each of these yarns. The yarns can be spun in the Z or S direction with a weaving twist multiple being preferred.

In addition, the above-described yarn can be colored, if desired. If colored, the yarn should be dope dyed in the resin solution. Pigments are useful that are insoluble in water to produce the highest quality light sublimentation and mark-off resistance. Fabric can be formed by weaving or by other well known techniques. For example, yarns can be intermingled in a perpendicular fashion or can be woven, or yarns can be single knit, double knit, interlocked, warped knit, or crocheted, as desired. It is even possible to bypass the yarn formation method and produce a nonwoven fabric directly from the fiber which is commonly referred to as either air laid, dry laid, wet laid, hydroentangled, thermo bonded, or chemical bonded.

Generally, the non-woven fabrics of the present invention are made as follows. A chosen amount of the polymer fibers are formed into a fabric layer of about 0.02 to 30 mil thickness or having a density of about 10–100 g/m$^2$.

The woven fabrics of the invention are made from yarns which are woven into fabrics using conventional weaving procedures. However, in order to be formed, the fibers which form such yarns (as well as being used to form the non-woven fabrics) must be pretreated with a spin finish. As described herein, a "spin finish" is generally composed of three ingredients: an antistatic agent (e.g., polyethylene oxide ("POE") alkylethersulfate sodium and alkylphosphate potassium), a lubricant/antifriction agent (e.g., glyceryl stearate), and a cohesion agent. (e.g., POE alkylether) By way of example only, the components may be formulated as an 80/10/10 mixture of antistatic/cohesion/antifriction agent which is diluted with approximately an equal amount of water before application to, .e.g., poly(vinyl) alcohol fibers. Even though the spin finish comprises only about 0.2% to about 0.5% by weight of the final yarn, at least some of the components are hydrophobic and thus are believed to reduce absorbency and lead to poor hand-feel of woven fabrics of poly(vinyl) alcohol that have been treated with the spin finish. As a reference, poly(vinyl) alcohol fabric with such spin finish has an absorbency value of about 80% and feels slick to the touch. On the other hand, cotton towels that have been washed and bleached (which removes finishing agents thereon) have a superior absorbency value of 120% for weaves compatible with surgical uses and do not suffer from slickness or otherwise poor hand-feel.

Unfortunately, unlike cotton, bleaching and washing of (un-sized) poly(vinyl) alcohol based fabrics, including, but not limited to, surgical fabrics, is not feasible because such procedures either solubilize or degrade the fabric unacceptably. Therefore, the spin finish generally remains on the poly(vinyl) alcohol based fabrics because, prior to the present invention, there was no practical and effective way to remove or alter the spin finish.

In accordance with the present invention, the above-referenced fabrics have been enhanced by the following procedures.

The first procedure is to post-process the material by compacting or microcreping the finished fabric. The microcreping involves creating regularly spaced crimps in the surface of the fabric. One such method of microcreping or compacting the fabric is to use a 124" Micrex Microcreper line (MXS-231, Micrex Corp., Walpole, Mass.) machine. Pursuant to the present invention, the hand-feel of absorbent fabrics can be improved by processing roll material of the raw fabric in such a Micrex machine. By manipulating line speed, roll temperature and line speed, the degree of compaction (%) is controlled by the operator. For the purposes of the present invention, a compaction level of from 0 to about 30% is desirable. For such compaction, line speed was maintained between about 33 and about 100 yds./min. while the roll temperature was maintained from 400 to 450° F. The results shown below in Table I demonstrate an increase in absorbency over untreated stock and a marked improvement in hand-feel. The data were generated using roll stock using 26" wide samples.

TABLE I

| Sample | Compaction % | Speed | Temp. | % Absorbency |
| --- | --- | --- | --- | --- |
| 1 | 5 | 33 | 400 | 84.6 |
| 2 | 5 | 100 | 400 | 87.5 |
| 3 | 5 | 33 | 450 | 74.8 |
| 4 | 10 | 33 | 400 | 89.8 |
| 5 | 15 | 33 | 400 | 82.8 |
| 6 | 15 | 100 | 400 | 85.3 |
| 7 | 15 | 33 | 450 | 62.9 |
| 8 | 20 | 33 | 400 | 78.0 |
| 9 | 20 | 100 | 400 | 71.4 |
| 10 | 30 | 33 | 400 | 60.9 |
| 11 | n/a | n/a | n/a | 77.8 |

In addition to compaction or microcreping as described above, the fabrics described herein can be further processed or alternately processed using an electrical treatment method. Roll samples were passed through a "corona treatment" or "electrical discharge treatment" machine (PowerHouse™ machines using PowerSource™ corona generators, Corona Designs, Inc., Garland, Tex.) at 1, 2, 3, 4, 5, 6, 7, and 7.5 kW of power supply. No shrinkage of the samples was noted. Corona treatment using machines having power supplies in the range of 1 to 5 kW was preferred, with 4–5 kW being even more preferable. Treatment using equipment operating at above 5 kW caused undesirable physical changes to the substrate fabric. By way of example only, in one test, 16" wide roll samples were passed through the corona treater having a 4 kW power supply (9.6 KHZ, 240/480 V, three phase) operating at 100% at 20 ft./min. with an air gap of 0.060". In another example, 16" wide roll samples were passed through the corona treated having a 5 kW power supply operating at 65% at 20 ft./min. with an air gap of 0.106". Based upon the above kW range parameters, corona treatment at from about 40 watt-min./sq. ft. to 190 watt-min./sq. ft., preferably 150 to 190 watt-min./sq. ft., was found to be sufficient.

Corona treatment involves subjecting a substrate to a strong electric field which, it is believed, acts to ionize the gas layer around the substrate. However, rather than arcing, because a substrate is present, an incomplete breakdown of the intervening gases occurs. Instead of a very hot localized arc, there is a cooler, diffuse glow between the electrodes which has been described as a "corona."

The effect of corona treatment is one or more of the following 1) physical, such as micropitting; 2) electrostatic, such as via an electret effect; and 3) chemical, such as oxidation at the surface of the substrate. Without wishing to be bound by theory, it is believed that corona treatment of the poly(vinyl) alcohol fibers of the present invention serves to volatilize, vaporize, or degrade the surface finishing or spin finish compounds. It is believed that these compounds are responsible for the poor hand feel and lower absorbency of untreated poly(vinyl) alcohol articles compared to the articles of the present invention.

Corona treatment uses a treater station having a roll with an insulating coating that carries the substrate web thereon. The core of the roll is electrically grounded. An electrode is spaced far enough from the roll surface to allow the substrate web to pass through the gap without touching the electrode. The air gap is generally on the order of 1.5 mm. Minimization of the air gap lowers the voltage required to provide ionization at the minimum. Stations can be built with two rolls and two electrodes so that both sides of the substrate can be treated at once.

If the substrate is sufficiently thick to withstand the desired voltage and has an edge trim, the substrate itself may form the insulator and a bare ground roll is sufficient. Otherwise, the roll must be coated.

Most such treater stations have a method of retracting the electrode or the roll to allow a wider gap for ease of thread up. The corona process generates ozone which is a hazard that is contained by enclosing the station and providing for neutralization and removal of the ozone.

Generally, the determination of the amount of power to treat a material is determined by testing various samples.

Table II shows the absorbency readings for surgical fabrics treated with the above-described corona treatment procedure at various power levels.

TABLE II

| Sample | 1 kW | 2 kW | 3 kW | 4 kW |
|---|---|---|---|---|
| Avg. Absorbency (%) | 91.4 | 90.6 | 101.2 | 109.3 |
| Abs. SD | 5.3 | 5.3 | 4.7 | 4.3 |
| Abs. Max. | 100.0 | 98.6 | 105.6 | 115.5 |
| Abs. Min. | 85.6 | 81.9 | 93.2 | 103.9 |
| Avg. Mass (g) | 50.6 | 50.6 | 47.1 | 46.7 |
| Mass SD | 1.3 | 1.1 | 0.4 | 1.1 |
| Mass Max. | 52.1 | 52.4 | 47.6 | 48.9 |
| Mass Min. | 49.2 | 49.6 | 46.5 | 45.6 |

SD = standard deviation
Min. = minimum
Max. = maximum
Abs. = absorbency

In addition, 16" wide roll stock of poly(vinyl) alcohol fiber based woven fabric was corona treated using a 4 kW power supply operating at 100% power, with the roll running at 20 ft./min. Roll # 1 was corona treated on both sides, while Roll # 2 was corona treated on one side only. Roll # 2 samples were folded so that the treated side was on the outside when tested for absorbency. Initial absorbency was tested using the Flynn method and the results are shown in Table III. The data demonstrate increased absorbency of all fabrics that were corona treated over the untreated substrate absorbency value of about 80%.

TABLE III

| Sample ID | Pre weight (g.) | Post weight (g.) | Water Abs. (g) | Abs. (%) |
|---|---|---|---|---|
| Roll #1 | | | | |
| 1 | 45.8 | 105.2 | 59.4 | 129.7 |
| 2 | 46.8 | 100.8 | 54.0 | 115.4 |
| 3 | 50.0 | 109.6 | 59.6 | 119.2 |
| Avg. | 47.5 | 105.2 | 57.7 | 121.4 |
| Roll #2 | | | | |
| 1 | 50.5 | 106.0 | 55.5 | 109.9 |
| 2 | 50.6 | 102.5 | 51.9 | 102.6 |
| 3 | 53.5 | 104.6 | 51.1 | 95.5 |
| Avg. | 51.5 | 104.4 | 52.8 | 102.7 |

Table II shows surprisingly increased absorbency for corona treatments above the inherent roll absorbency of 80%. In addition, without wishing to be bound by theory, it has been observed that at least a portion of the spin finish has been degraded, volatilized or vaporized by the corona treatment and, therefore, the resulting fabric is more hydrophilic and exhibits increased absorbency.

The present invention therefore provides, in one embodiment, a method for enhancing the absorbency, hand-feel, or both of an article comprised of fibers having a finish thereon, the method comprising subjecting the article to corona treatment for a period of time sufficient to enhance the absorbency, hand-feel, or both of the article. The sufficiency of the period of time is determined by measuring the absorbency or observing the hand-feel (or both the absorbency and hand-feel) of the article and comparing it to the unprocessed article, wherein any improvement in absorbency or hand-feel indicates that a sufficient period of time has transpired. In a preferred embodiment, especially for treating a poly(vinyl) alcohol based substrate, the corona treatment electric field power is from 1 to 5 kW, even more preferably from 4 to 5 kW.

In another embodiment, the invention provides an article produced by subjecting a substrate comprised of fibers having a finish thereon to corona treatment using an electric field for a period of time sufficient to enhance the absorbency, hand-feel, or both of the substrate.

In yet another embodiment, the invention provides a method of disposing of an article produced by subjecting a hot-liquid soluble, cold-liquid insoluble substrate comprised of fibers having a finish thereon to corona treatment for a period of time sufficient to enhance the absorbency, hand-feel, or both of the substrate, the method comprising contacting the article with a hot liquid for a period of time sufficient to disperse or dissolve the article. In a preferred embodiment, the liquid is water.

In yet further embodiment, the invention involves microcreping the substrate in at least one direction from about 1 to about 30%. In addition, in a preferred embodiment, the method involves microcreping the substrate in at least one direction about 20%.

In further embodiments of the articles, the fabric layer can have a density of from 20 to about 120 $g/m^2$, more preferably of from 40 to about 100 $g/m^2$, even more preferably from about 60 to about 80 $g/m^2$, and most preferably about 70 $g/m^2$. In yet another embodiment, the fabric layer has a thickness of from about 0.02 mils to about 60 mils.

In one embodiment, the fabric comprises poly(vinyl) alcohol. In a preferred embodiment, the poly(vinyl) alcohol is a greater than 95% saponified poly vinyl acetate, more preferably greater than 98% saponified poly vinyl acetate, even more preferably greater than 99% saponified poly vinyl acetate, and even more preferably is greater than 99.99% saponified poly vinyl acetate. In one embodiment, the poly (vinyl) alcohol fibers are composed of no more than 0.5% sodium acetate by weight and 0.1% methyl alcohol by weight and have an average degree of polymerization of between approximately 300 to 3000.

For fabrics having dissolution temperatures of 70° C. to 90° C. and above, the polyvinyl alcohol fibers are produced by a process of dope extrusion (also referred to as "wet spinning", "solution spinning" or "wet/solution spinning") and then treated with heat and stretching. Alternatively, such articles may be produced by melt spinning or hydrogel spinning followed by heating and stretching. For articles having dissolution temperatures of from about 37° C. to 70° C., the fibers are produced by either melt spinning or hydrogel spinning followed by heating and stretching as described herein.

In a preferred embodiment, the polyvinyl alcohol is a produced from a greater than 80% saponified polyvinyl acetate. In yet another embodiment, the polyvinyl alcohol is a produced from a greater than 98% saponified polyvinyl acetate. In a further embodiment, the polyvinyl alcohol is a produced from a greater than 99% saponified polyvinyl acetate.

In an alternate embodiment, the degree of polymerization of the fibers is from about 300 to about 3000. In a further embodiment, the degree of polymerization of the fibers is from about 700 to about 2000. In yet another further embodiment, the degree of polymerization of the fibers is from about 1300 to about 2000.

In a further embodiment, the polyvinyl alcohol has a degree of crystallinity of at least about 0.20. In a further embodiment, the polyvinyl alcohol has a degree of crystallinity of at least about 0.40. In yet a further embodiment, the polyvinyl alcohol has a degree of crystallinity of at least about 0.70. Moreover, in a further embodiment, the polyvinyl alcohol has a degree of orientation of at least about 0.20. In a further embodiment, the polyvinyl alcohol has a degree of orientation of at least about 0.40. In yet a further embodiment, the polyvinyl alcohol has a degree of orientation of at least about 0.50.

In yet a further embodiment, the polyvinyl alcohol is only water soluble at temperatures above about 50° C. In another preferable embodiment, the polyvinyl alcohol is only water soluble at temperatures above about 70° C. In a more preferably embodiment, the polyvinyl alcohol is only water soluble at temperatures above about 90° C.

Other suitable hot liquid soluble, cold liquid insoluble materials, such as poly vinyl alcohol materials, are described in detail in U.S. Pat. Nos. 5,181,966, 5,181,967, and 5,207,837, the contents of which are hereby incorporated by this reference. As mentioned above, other synthetic fabrics such as rayon and polyester fabrics would benefit in absorbency, hand-feel, or both from the processing methods of the present invention. In addition, various natural fibers, such as unwashed cotton fibers, could be enhanced by the treatments described herein.

In addition to these articles, the present invention also provides a disposal method applicable to the articles. In particular, the present invention provides a method of disposing of the articles of the invention, where the article is soluble in a liquid when the liquid is hot and insoluble in the liquid when the liquid is cold. The method involves contacting the article with a sufficiently hot liquid for a sufficient period of time to disperse or dissolve substantially the article. Thus, if the liquid is water and the sufficient heat is, e.g., 90° C., then boiling the article in water (at 100° C.) would thereby disperse or dissolve substantially the article. However, other solvents may be used and materials may be chosen so that the articles are disposable as described herein.

In a preferred embodiment, the articles to be disposed are introduced into a washing machine and are agitated in hot water for a period of time sufficient to effect disposal. Preferably, the hot water is of a temperature of at least 50° C., more preferably at least 90° C., and even more preferably at least 95° C. In addition, the period of time in the machine is from about 2 minutes to about 40 minutes, and more preferably is from about 10 to about 30 minutes. Depending upon the composition of the article, the runoff from the machine may be released to the sewage system (if all biodegradable) or the insoluble or non-biodegradable components may be reclaimed via filtration or dehydration or other known separating processes.

The following examples are put forth so as to provide those of ordinary skill in the art with a complete disclosure and description of how the compounds articles claimed herein are made, used and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and is at room temperature, and pressure is at or near atmospheric.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method for enhancing the absorbency, hand-feel or both of an article or fabric comprised of fibers having a finish thereon; the method comprising subjecting the article or fabric to corona treatment for a period of time sufficient to enhance the absorbency, hand-feel, or both of the article or fabric, wherein (i) the article or fabric is prepared by (a) providing a fibrous material, (b) pretreating the fibrous material with a finish composition, and (c) forming the pretreated fibrous material into an article or fabric; and (ii) the finish composition comprises an antistatic agent, a lubricant or antifriction agent, and a cohesion agent.

2. The method of claim 1, further comprising microcreping the article or fabric in at least one direction from about 1 to about 30%.

3. The method of claim 1, further comprising microcreping the article or fabric in at least one direction about 20%.

4. The method of claim 1, wherein the fibers are rayon fibers, polyester fibers, poly(vinyl) alcohol fibers, or a mixture thereof.

5. The method of claim 1, wherein the fibers are cotton fibers.

6. The method of claim 1, wherein the article is a surgical fabric.

7. The method of claim 1, wherein the article is a gauze, towel, or drape.

8. The method of claim 1, wherein the article is a mask.

9. The method of claim 1, wherein the article is a sponge.

10. The method of claim 1, wherein the corona treatment uses from 1 to 5 kW of power.

11. The method of claim 1, wherein the corona treatment is at from 40 to 190 watt-min./sq. ft.

12. The method of claim 1, wherein the article or fabric is comprised of poly(vinyl) alcohol fibers.

13. The method of claim 12, wherein the poly(vinyl) alcohol is produced from a greater than 80% saponified polyvinyl acetate.

14. The method of claim 12, wherein the poly(vinyl) alcohol is produced from a greater than 99% saponified polyvinyl acetate.

15. The method of claim 12, wherein the degree of polymerization of the poly(vinyl) alcohol of the fibers is from 1300 to 2000.

16. The method of claim 12, wherein the poly(vinyl) alcohol has a degree of crystallinity of at least 0.70.

17. The method of claim 12, wherein the poly(vinyl) alcohol has a degree of orientation of at least 0.50.

18. The method of claim 12, wherein the poly(vinyl) alcohol is only water soluble at temperatures above 50° C.

19. The method of claim 1 wherein the antistatic agent comprises polyethylene oxide alkylethersulfate sodium or polyethylene oxide alkylphosphate potassium; the lubricant/antifriction agent comprises glyceryl stearate; and the cohesion agent comprises a polyethylene oxide alkylether.

20. An article or fabric comprising fibers having a finish thereon, wherein (i) the article or fabric is prepared by (a) providing a fibrous material, (b) pretreating the fibrous material with a finish composition, (c) forming the pretreated fibrous material into an article or fabric, and (d) subjecting the article or fabric to corona treatment for a period of time sufficient to enhance the absorbency, hand-feel, or both of the article or fabric; and (ii) the finish composition comprises an antistatic agent, a lubricant or antifriction agent, and a cohesion agent.

21. The article or fabric of claim 20, further produced by microcreping the article or fabric in at least one direction from about 1 to about 30%.

22. The article or fabric of claim 20, wherein the article is a surgical fabric.

23. The article or fabric of claim 20, wherein the article is a gauze, towel, or drape.

24. The article or fabric of claim 20, wherein the article is a mask.

25. The article or fabric of claim 20, wherein the article is a sponge.

26. The article or fabric of claim 20, wherein the corona treatment uses from 1 to 5 kW of power.

27. The article or fabric of claim 20, wherein the corona treatment is at from 40 to 190 watt-min./sq. ft.

28. The article or fabric of claim 20, further produced by microcreping the article or fabric in at least one direction about 20%.

29. The article or fabric of claim 20, wherein the article or fabric is comprised of poly(vinyl) alcohol fibers.

30. The article or fabric of claim 20 wherein the antistatic agent comprises polyethylene oxide alkylethersulfate sodium or polyethylene oxide alkylphosphate potassium; the lubricant/antifriction agent comprises glyceryl stearate; and the cohesion agent comprises a polyethylene oxide alkylether.

31. A method of disposing of an article produced by subjecting a hot-liquid soluble, cold-liquid insoluble article comprised of fibers having a finish thereon to corona treatment for a period of time sufficient to enhance the absorbency, hand-feel, or both of the article, the method comprising contacting the article with a hot liquid for a period of time sufficient to disperse or dissolve the article.

32. The method of claim 31, wherein the liquid is water.

33. The method of claim 31, wherein the article is a surgical fabric.

34. The method of claim 31, wherein the article is a gauze, towel, or drape.

35. The method of claim 31, wherein the article is a mask.

36. The method of claim 31, wherein the article is a sponge.

37. The method of claim 31, wherein the corona treatment uses from 1 to 5 kW of power.

38. The method of claim 31, wherein the corona treatment is at from 40 to 190 watt-min./sq. ft.

39. The method of claim 31, wherein the article is comprised of poly(vinyl) alcohol fibers.

* * * * *